United States Patent [19]

Wilde et al.

[11] Patent Number: 5,032,574

[45] Date of Patent: Jul. 16, 1991

[54] NOVEL ANTIMICROBIAL PEPTIDE

[75] Inventors: Craig G. Wilde; Joseph E. Griffith, both of Foster City; Marian N. Marra, San Mateo; Randal W. Scott, Sunnyvale, all of Calif.

[73] Assignee: Invitron Corporation, St. Louis, Mo.

[21] Appl. No.: 199,206

[22] Filed: May 26, 1988

[51] Int. Cl.$^5$ .............................................. C07K 7/10
[52] U.S. Cl. ..................................... 514/012; 530/324
[58] Field of Search ............................ 530/324; 514/12

[56] References Cited

U.S. PATENT DOCUMENTS 4,705,777  11/1987  Lehrer ................................... 514/2

*Primary Examiner*—Margaret Moskowitz
*Assistant Examiner*—Nina Ossanna
*Attorney, Agent, or Firm*—John P. White

[57] ABSTRACT

This invention provides a purified polypeptide useful as an antimicrobial agent. This purified polypeptide has been derived from human granulocytes, and has a molecular weight of about 3,700 daltons and the N-terminal amino acid sequence val-cys-ser-cys-arg-leu-val-phe-cys-arg-arg-thr-glu- leu-arg-val-gly-asn-cys-leu-ile-gly-gly-val-ser-phe-thr-try-cys-thr-arg-val. This invention also provides methods for producing this polypeptide, pharmaceutical compositions containing the polypeptide, and uses thereof.

6 Claims, 8 Drawing Sheets

N-TERMINAL AMINO ACID SEQUENCE OF PEAK 1

| RESIDUE | HNP1 AND 3* | YIELD IN PICOMOLES | HNP2* | YIELD IN PICOMOLES |
|---|---|---|---|---|
| 1 | ALA/ASP | 518/86 | — | — |
| 2 | — | — | TYR | 581 |
| 3 | TYR | 640 | — | — |
| 4 | — | — | ARG | 151 |
| 5 | ARG | 65 | ILE | 460 |
| 6 | ILE | 757 | PRO | 348 |
| 7 | PRO | 427 | ALA | 363 |
| 8 | ALA | 310 | — | — |
| 9 | — | — | ILE | 353 |
| 10 | ILE | 493 | ALA | 224 |
| 11 | ALA | 607 | GLY | 267 |
| 12 | GLY | 450 | GLU | 204 |
| 13 | GLU | 105 | ARG | 31 |
| 14 | ARG | 446 | — | — |
| 15 | ARG | 424 | TYR | 258 |
| 16 | TYR | 479 | GLY | 229 |
| 17 | GLY | 295 | THR | 105 |
| 18 | THR | 232 | — | — |
| 19 | — | — | ILE | 177 |
| 20 | ILE | 301 | TYR | 175 |
| 21 | TYR | 271 | GLN | 122 |
| 22 | GLN | 225 | GLY | 115 |
| 23 | GLY | 144 | ARG | 52 |
| 24 | ARG | 101 | LEU | 80 |
| 25 | LEU | 83 | TRP | 15 |
| 26 | TRP | 34 | ALA | 24 |
| 27 | ALA | 109 | PHE | 46 |
| 28 | PHE | 90 | — | — |

*As defined in Selsted, M.E. et al. (1985) J. Clin. Invest. 76, 1436

FIGURE 3

N-TERMINAL AMINO ACID SEQUENCE OF PEAK 2

| RESIDUE | PEAK 2 | YIELD IN PICOMOLES |
|---|---|---|
| 1 | VAL | 212 |
| 2 | — | — |
| 3 | SER | 85 |
| 4 | — | — |
| 5 | ARG | 46 |
| 6 | LEU | 116 |
| 7 | VAL | 133 |
| 8 | PHE | 135 |
| 9 | — | — |
| 10 | ARG | 72 |
| 11 | ARG | 92 |
| 12 | THR | 88 |
| 13 | GLU | 62 |
| 14 | LEU | 82 |
| 15 | ARG | 47 |
| 16 | VAL | 42 |
| 17 | GLY | 69 |
| 18 | ASN | 68 |
| 19 | — | — |
| 20 | LEU | 48 |
| 21 | ILE | 43 |
| 22 | GLY | 46 |
| 23 | GLY | 59 |
| 24 | VAL | 30 |
| 25 | SER | 25 |
| 26 | PHE | 26 |
| 27 | THR | 21 |
| 28 | TYR | 25 |
| 29 | — | — |
| 30 | — | — |
| 31 | THR | 9 |
| 32 | ARG | 8 |
| 33 | VAL | 4 |

FIGURE 4

COMPARISON OF PEAK 2 TO HUMAN, RABBIT, AND GUINEA PIG DEFENSINS

|  | 1 |  |  |  | 5 |  |  |  |  | 10 |  |  |  |
|---|---|---|---|---|---|---|---|---|---|---|---|---|---|---|
| PEAK 2 | VAL | CYS | SER | CYS | ARG | LEU | VAL | PHE | CYS | ARG | ARG | THR | GLU | |
| HNP-1** | | ALA | CYS | TYR | CYS | ARG | ILE | PRO | ALA | CYS | ILE | ALA | GLY | GLU |
| HNP-2 | ASP | CYS | TYR | CYS | ARG | ILE | PRO | ALA | CYS | ILE | ALA | GLY | GLU | |
| HNP-3 | VAL | CYS | TYR | CYS | ARG | ILE | PRO | ALA | CYS | ILE | ALA | GLY | GLU | |
| RNP-1*** | VAL | VAL | CYS | ALA | CYS | ARG | ARG | ALA | LEU | CYS | LEU | PRO | ARG | GLU |
| RNP-2 | VAL | VAL | CYS | ALA | CYS | ARG | ARG | ALA | LEU | CYS | LEU | LEU | ARG | GLU |
| RNP-3a | GLY | ILE | CYS | ALA | CYS | ARG | ARG | ARG | PHE | CYS | PRO | PRO | SER | GLU |
| RNP-3b | GLY | ARG | CYS | VAL | CYS | ARG | LYS | GLN | 2LEU* | CYS | SER | ASN | ARG | GLU |
| RNP-4 | VAL | SER | CYS | THR | CYS | ARG | ARG | PHE | SER | CYS | GLY | TYR | GLY | GLU |
| RNP-5 | VAL | PHE | CYS | THR | CYS | ARG | GLY | PHE | LEU | CYS | GLY | PHE | GLY | GLU |
| GPNP**** | ARG | ARG | CYS | ILE | CYS | THR | THR | ARG | THR | CYS | ARG | SER | PRO | TYR |

|  |  | 15 |  |  |  |  | 20 |  |  |  |  | 25 |  |  |
|---|---|---|---|---|---|---|---|---|---|---|---|---|---|---|
| PEAK 2 | LEU | ARG | VAL | GLY | ASN | CYS | LEU | ILE | GLY | VAL | ARG | SER | PHE | THR |
| HNP-1 | ARG | ARG | TYR | GLY | THR | CYS | ILE | TYR | GLN | GLY | ARG | LEU | TRP | ALA |
| HNP-2 | ARG | ARG | TYR | GLY | THR | CYS | ILE | TYR | GLN | GLY | ARG | LEU | TRP | ALA |
| HNP-3 | ARG | ARG | TYR | GLY | THR | CYS | ILE | TYR | GLN | GLY | ARG | LEU | TRP | ALA |
| RNP-1 | ARG | ARG | ALA | GLY | PHE | CYS | ARG | ILE | ARG | GLY | ARG | ILE | HIS | PRO |
| RNP-2 | ARG | ARG | ALA | GLY | PHE | CYS | ARG | ILE | ARG | GLY | ARG | ILE | HIS | PRO |
| RNP-3a | ARG | PHE | SER | GLY | TYR | CYS | ARG | VAL | ASN | ARG | ALA | ARG | TYR | VAL |
| RNP-3b | ARG | ARG | ILE | GLY | ASP | CYS | LYS | ILE | ARG | VAL | VAL | ARG | PHE | PRO |
| RNP-4 | ARG | ALA | SER | GLY | SER | CYS | THR | VAL | ASN | ARG | VAL | ARG | HIS | THR |
| RNP-5 | ARG | ALA | SER | GLY | SER | CYS | THR | ILE | ASN | ARG | VAL | VAL | HIS | THR |
| GPNP | ARG | ARG | LEU | GLY | THR | CYS | ILE | PHE | GLN | ASN | ARG | VAL | TYR | THR |

Figure 4 (Continued)

| PEAK 2 | | TYR | CYS | CYS (30) | THR | ARG | VAL |
|---|---|---|---|---|---|---|---|
| HNP-1 | PHE | CYS | CYS | | | | |
| HNP-2 | PHE | CYS | CYS | | | | |
| HNP-3 | PHE | CYS | CYS | | | | |
| RNP-1 | LEU | CYS | CYS | ARG | ARG | | |
| RNP-2 | LEU | CYS | CYS | ARG | ARG | | |
| RNP-3a | ARG | CYS | CYS | SER | ARG | ARG | |
| RNP-3b | PHE | CYS | CYS | PRO | ARG | | |
| RNP-4 | LEU | CYS | CYS | ARG | ARG | | |
| RNP-5 | LEU | CYS | CYS | ARG | | | |
| GPNP | PHE | CYS | CYS | | | | |

\* LEU — leu bond expressed as 21eu
\*\* HNP — human neutrophil peptide
\*\*\* RNP — rabbit neutrophil peptide
\*\*\*\*GPNP — guinea pig neutrophil peptide

FIGURE 5

AMINO ACID COMPOSITION
COMPARISON BETWEEN PEAK 1 AND PEAK 2

|     | PEAK 1 | PEAK 2 | DIFFERENCES SQUARED |
|-----|--------|--------|---------------------|
| ASP | 0.97   | 2.39   | 2.02                |
| GLU | 5.41   | 2.44   | 8.82                |
| SER | 0.00   | 4.80   | 23.04               |
| GLY | 10.02  | 7.66   | 5.57                |
| HIS | 0.00   | 0.00   | 0.00                |
| ARG | 17.24  | 14.74  | 6.25                |
| THR | 2.98   | 8.26   | 27.88               |
| ALA | 9.64   | 0.25   | 88.17               |
| PRO | 4.42   | 0.00   | 19.54               |
| TYR | 6.04   | 2.78   | 10.63               |
| VAL | 0.33   | 10.82  | 110.04              |
| MET | 0.00   | 0.00   | 0.00                |
| ILE | 7.32   | 2.23   | 25.91               |
| LEU | 2.95   | 6.71   | 14.14               |
| PHE | 3.02   | 4.56   | 2.37                |
| LYS | 0.00   | 0.00   | 0.00                |

SIMILARITY INDEX = 344.87

FIGURE 6

COMPARISON OF MICROBICIDAL ACTIVITY OF GRANULOCYTE PEAK 1 AND GRANULOCYTE PEAK 2

|  |  | E. COLI | S. FAECALIS | C. ALBICANS |
|---|---|---|---|---|
| PEAK 1 (µg) | 90% KILL | >3.6 | >3.6 | >3.6 |
|  | 50% KILL | 0.7 | >3.6 | 1.2 |
| PEAK 2 (µg) | 90% KILL | 0.25 | 0.04 | 0.9 |
|  | 50% KILL | 0.02 | 0.02 | 0.2 |

FIGURE 7

EFFECT OF DETERGENTS ON MICROBICIDAL ACTIVITY OF GRANULOCYTE PEAK 1 AND GRANULOCYTE PEAK 2

GREATEST DILUTION TO GIVE 90% KILL

|  | NO DETERGENT | .02% TWEEN 20 | 1% NP40 |
|---|---|---|---|
| PEAK 1 | | | |
| E. COLI | 40 | 80 | 80 |
| S. FAECALIS | <20 | <20 | 80 |
| C. ALBICANS | 20 | 80 | 20 |
| PEAK 2 | | | |
| E. COLI | 40 | >160 | >160 |
| S. FAECALIS | 40 | 80 | >160 |
| C. ALBICANS | <20 | 20 | <20 |

NOVEL ANTIMICROBIAL PEPTIDE

BACKGROUND OF THE INVENTION

Granulocytes play an important role in host resistance to bacterial, fungal and parasitic pathogens. This resistance is effected through at least two different pathways. In the oxygen dependent pathway, the granulocytes produce toxic oxygen metabolites which participate in killing the invading pathogen. The second pathway is oxygen independent and consists of production and storage of proteins which have potent antimicrobial activity. The importance of these granulocytic defense mechanisms is indicated by the finding that neutropenic patients are unusually susceptible to long term infections, which are sometimes fatal. A number of microbicidal proteins and peptides have been demonstrated in granulocytes, including eosinophil major basic protein, eosinophil cationic protein, bacteria permeability increasing factor and a group of small antibiotic peptides termed defensins which have been isolated from humans (M. E. Selsted et al., J. Clin. Invest. 76: 1436 (1985)), rabbits (M. E. Selsted et al., J. Biol. Chem. 260: 4579 (1985)), and guinea pigs (M. E. Selsted et al., Infec. Immun. 55: 2281 (1987)).

Figure 4:
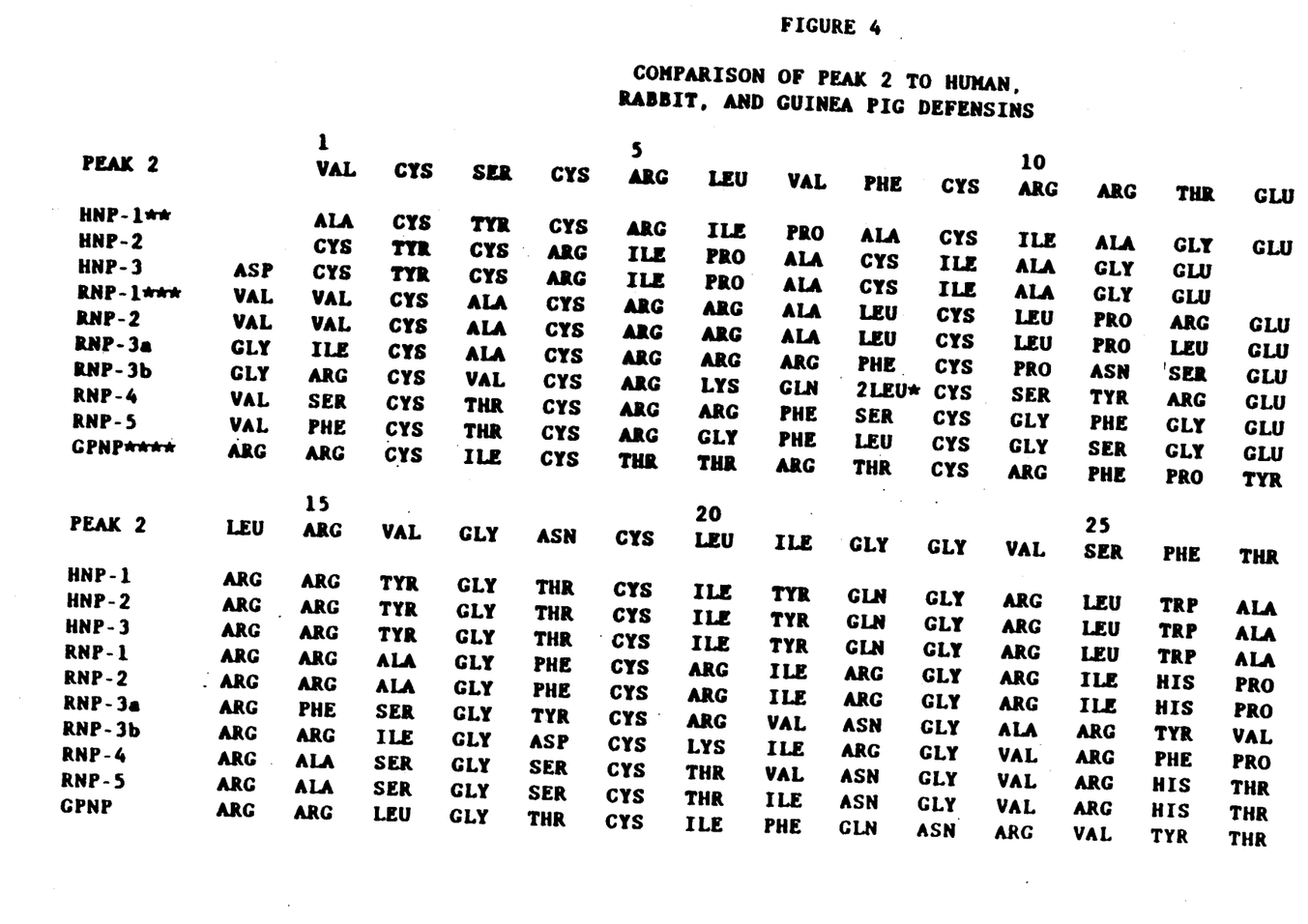

The reported sequences of the known human, rabbit and guinea pig defensins are shown in FIG. 4. In addition, U.S. Pat. No. 4,543,252, issued Sept. 24, 1985 and assigned to the Regents of the University of California discloses cationic oligopeptides of up to about 35 amino acids which have microbicidal activity. A comparison of various defensin sequences show that six cysteines are completely conserved among human, rabbit, and guinea pig defensins. It is believed that these residues may be involved in maintenance of secondary structure. In addition, five other residues (2 arg, 2 gly, glu) are conserved in all human and rabbit defensins, three of which are also conserved in guinea pig defensin.

A single difference among human defensins at the N-terminus is sufficient to produce significant changes in microbicidal potency and selectivity (R. I. Lehrer et al., Infect. Immun. 42: 10 (1983)). Moreover, the larger differences among the rabbit defensins drastically alter their bactericidal activity (M. E. Selsted et al., Infect. Immun. 45: 150 (1984)), their candidacidal activity (M. E. Selsted et al., Infect. Immun. 49: 202 (1985)) and their tumor cell cytolytic activity (A. Lichtenstein, Blood 68: 1407 (1986)). Therefore, although sequence conservation suggests certain secondary structures may be necessary for activity, it is clear that these structures are not sufficient for activity and that the potency and the specificity of the peptides are almost solely determined by sequence in non-conserved regions.

The polypeptides of the subject invention shares the cysteine backbone of defensins, but diverges radically in its remaining sequence. It is different in 16 of 33 positions from any of the human or rabbit defensins, and therefore would be expected to differ widely in activity. Moreover, 22 of 33 positions differ from described human defensins. Human defensins are likely to be more important therapeutically because non-human defensins would expected to trigger undesirable immune responses.

When tested in vitro the purified polypeptide of this invention has been found to be significantly more active in microbicidal assays against *Escherichia coli*, *Streptococcus faecalis* and *Candida albicans* than a mixture of previously described defensins.

Finally, U.S. Ser. No. 125,684, filed Nov. 25, 1987, in the names of Joelle E. Gabay and Carl F. Nathan and assigned to Cornell Research Foundation and the Rockefeller University discloses a series of peaks obtained by reverse-phase, high pressure, liquid chromatography of an extract of human blood. Specifically, Peak 2 of FIG. 13 of U.S. Ser. No. 125,684 discloses the existence of the polypeptide of this invention. However, it is important to understand that the data presented in U.S. Ser. No. 125,684 is that of applicants on the subject application and that this application is assigned to the exclusive licensee of U.S. Ser. No. 125,684. Moreover, it is important to note that U.S. Ser. No. 125,684 does not disclose that Peak 2 of FIG. 13 which contains the polypeptide of this invention has antibacterial or antifungal activity and does not disclose the amino acid sequence or any other characterization of the polypeptide of Peak 2 of FIG. 13.

SUMMARY OF THE INVENTION

Figure 3:
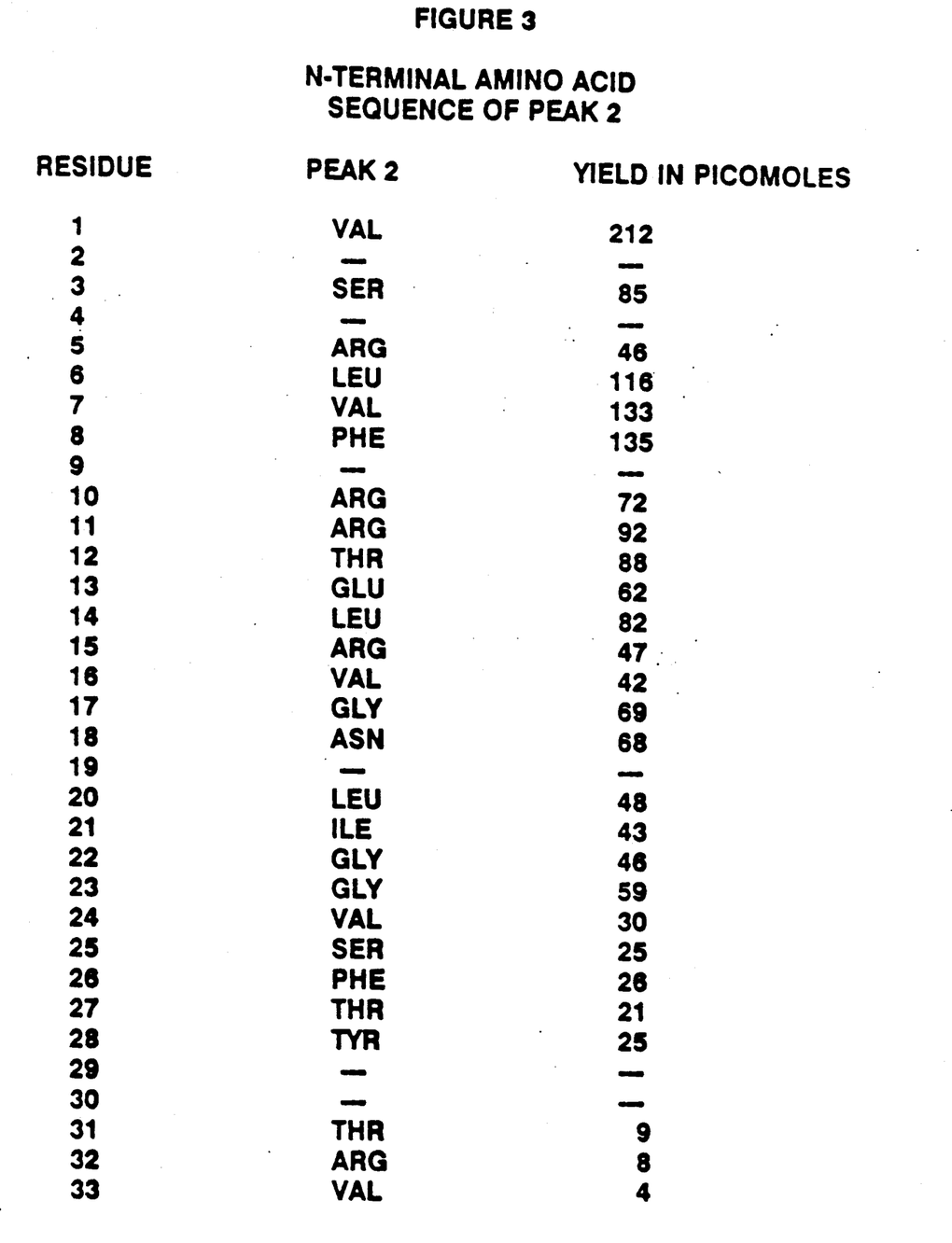

The present invention provides a purified polypeptide useful as an antimicrobial agent having a molecular weight of about 3,700 daltons and the N-terminal amino acid sequence shown in FIG. 3 or a biologically active portion thereof. The polypeptide has antimicrobial activity against gram negative and gram positive bacteria and against fungi.

The present invention also provides a method of preparing the purified polypeptide which comprises purification of the polypeptide from granules which in turn are obtained from substantially pure, human granulocytes.

The present invention also provides a pharmaceutical composition comprising an effective bacterial-killing or fungal-killing amount of the purified polypeptide and a pharmaceutically acceptable carrier and the use of this composition to treat subjects having bacterial or fungal infections.

The invention further provides a pharmaceutical composition comprising the purified polypeptide incorporated into a pharmaceutically acceptable liposome and the use of such a composition to treat a subject having a bacterial or fungal infection.

BRIEF DESCRIPTION OF THE FIGURES

FIG. 2—Sequencing Results for Granulocyte Peak 1

Amino acids identified at residues 1–28 by automated sequence analysis of granulocyte Peak 1 (FIG. 1).

FIG. 3—Sequencing Results for Granulocyte Peak 2

Amino acids identified at residues 1–33 by automated sequence analysis of granulocyte Peak 2 (FIG. 1).

FIG. 4—Sequence Comparison of Granulocyte Peak 2 and Human and Rabbit Defensins

Comparison of the N-terminal sequence determined for granulocyte Peak 2 with published sequences for human, rabbit, and guinea pig defensins.

FIG. 6—Comparison of Microbicidal Activity of Granulocyte Peak 1 and Granulocyte Peak 2

Granulocyte Peak 1 and granulocyte Peak 2 were assayed for antimicrobial activity in vitro as described in Methods. Amount of peptide required for 50% or 90% killing is compared. The number of microorganisms is as follows: *E. coli*, $6.4 \times 10^3$; *S. faecalis*, $2.0 \times 10^3$; *C. albicans*, $1.0 \times 10^3$.

FIG. 7

Effect of detergents on microbicidal activity of granulocyte Peak 1 and granulocyte Peak 2 is shown.

DETAILED DESCRIPTION OF THE INVENTION

The present invention provides a purified polypeptide useful as an antimicrobial agent which comprises a polypeptide having a molecular weight of about 3,700 and the N-terminal amino acid sequence val-cys-ser-cys- arg-leu-val-phe-cys-arg-arg-thr-glu-leu-arg-val-gly- asn-cys-leu-ilu-gly-gly-val-ser-phe-thr-tyr-cys-cys-thr-arg-val. The invention further provides biologically active fragments derived from this polypeptide, which, as will be readily appreciated by those skilled in the art, may be determined by preparing fragments of the polypeptide using conventional methods.

The invention also concerns DNA molecules which encode the polypeptide of this invention and biologically active fragments thereof and expression vectors which comprise such DNA molecules. Such DNA molecules may be readily prepared using an automated DNA sequence and the well-known codon amino acid relationship of the Genetic Code. Alternatively, such a DNA molecule may be obtained as genomic DNA or as cDNA using oligonucleotide probes and conventional methodologies.

Such DNA molecules may be incorporated into conventional expression vectors or specifically created expression vectors, including plasmids, which are adapted for expression of the DNA and production of the polypeptide in a suitable host such as bacterium, e.g., *Escherichia coli*, fungus cell, or mammalian cell.

The invention further provides a host vector system for producing a polypeptide having a molecular weight of about 3,700 and the N-terminal amino acid sequence described above, or a biologically active fragment thereof, which comprises a plasmid containing the DNA sequence encoding the polypeptide in a suitable host.

A method for producing a polypeptide having a molecular weight of about 3,700 and the N-terminal amino acid sequence val-cys-ser-cys-arg-leu-val-phe-cys-arg-arg- thr-glu-leu-arg-val-gly-asn-cys-leu-ilu-gly-gly-val-ser-phe-thr-tyr-cys-cys-thr-arg-val or a biologically active fragment thereof is also provided. The method comprises growing a host vector system comprising an expression vector which contains DNA encoding the polypeptide under suitable conditions permitting production of the polypeptide and recovering the resulting polypeptide from the host.

An alternative method of preparing the purified polypeptide of the invention is also provided. The method comprises:

a) treating human blood cells so as to separately obtain therefrom granulocytes b) treating the resulting granulocytes so as to recover therefrom granules;

c) treating the granules so recovered with an extracting agent at a pH less than about 4 so as to separately obtain soluble proteins from the granules;

d) recovering the soluble proteins so separated; and e) treating the soluble proteins so recovered so as to obtain the purified polypeptide.

In certain embodiments of the invention, the treatment of the soluble proteins comprises size exclusion chromatography, ion-exchange chromatography, or reverse-phase, high performance, liquid chromatography. It will be appreciated by one skilled in the art, however, that treatment of soluble proteins to purify polypeptides may be accomplished by many methods known to those skilled in the art, all of which are contemplated by this invention. Further, in one embodiment of the invention, the treatment of granulocytes so as to recover granules comprises density gradient centrifugation.

The invention also provides a composition which comprises the purified polypeptide in an amount effective to kill bacteria or fungi and a suitable carrier. Such composition may be used in numerous ways to combat bacteria or fungi, for example, in household or laboratory antimicrobial formulations using carriers well-known in the art.

The invention further provides a pharmaceutical composition for treating a human bacterial or fungal infection which comprises the purified polypeptide of the invention in an amount effective to treat a human bacterial or fungal infection and a pharmaceutically acceptable carrier.

It should be understood that the compositions of the present invention have activity against a wide variety of microorganisms, such as fungi, bacteria (both gram positive and negative), and protozoa and viruses. Different compositions will have differing degrees of activities towards different organisms. The peptides of the present invention may also be combined with other proteins to act as preservatives to protect the proteins against bacterial degradation. Alternatively, the subject polypeptides or compositions may be used as preservatives and disinfectants in a wide variety of formulations, such as contact lens solutions, ointments, shampoos, medicaments, foods, and the like. The amount of the polypeptide which is employed in the compositions may vary depending upon the nature of the other components, the degree of protection required and the intended use of the composition.

Where the polypeptides are to be used as antimicrobial agents, they can be formulated in buffered aqueous media containing a variety of salts and buffers. The salts will for the most part be alkali and alkaline earth halides, phosphates and sulfates, e.g., sodium chloride, potassium chloride or sodium sulfate. Various buffers may be used, such as citrate, phosphate, HEPES, Tris or the like to the extent that such buffers are physiologically acceptable to the host which is being treated.

Various excipients or other additives may be used, where the compounds are formulated as lyophilized powders, for subsequent use in solution. The excipients may include various polyols, inert powders or other extenders.

Depending on the nature of the formulation and the host, the subject compounds may be administered in a variety of ways. The formulations may be applied topically, by injection, e.g., intravenously, intra peritoneally, etc., nasopharyngeally, etc.

The invention further provides a method for killing bacteria or fungi which comprises contacting the bacteria or fungi with an effective amount of the compositions described above. Effective amounts may be readily determined by those skilled in the art.

The invention further provides a method for treating a subject having a bacterial or fungal infection which comprises administering to the subject an effective amount of the pharmaceutical composition described above.

In another aspect of the invention, the composition comprising the purified polypeptide of the invention in an amount effective to kill bacteria or fungi and a suitable carrier; and the pharmaceutical composition for treating a human bacterial or fun9al infection which comprises the purified polypeptide of the invention in an amount effective to treat a human bacterial or fungal infection and a pharmaceutically acceptable carrier may additionally comprise a detergent. The addition of a detergent to such compositions is useful to enhance the antibacterial or antifungal characteristics of the novel polypeptide of the invention. Although any suitable detergent may be used, the presently preferred detergent is a nonionic detergent, such as Tween 20 or 1% NP40.

The invention also provides a pharmaceutical composition for treating a human bacterial or fungal infection which comprises the purified polypeptide of the invention in an amount effective to treat a human bacterial or fungal infection incorporated into a pharmaceutically acceptable liposome.

It will be readily understood by those skilled in the art that any suitable pharmaceutically acceptable liposome may be used as a vehicle for the polypeptide of the present invention. Such liposomal compositions have activity against a wide variety of microorganisms similar to the activity of other compositions of this invention discussed in more detail above. Additionally, these compositions may be administered in a variety of conventional and well-known ways as is also discussed in greater detail above.

The Experimental Detail section which follows is set forth to aid in an understanding of the invention but is not intended to, and should not be construed to, limit in any way the invention as set forth in the claims which follow thereafter.

EXPERIMENTAL DETAILS

Methods

Isolation of Granulocytes

Buffy coats were obtained from local blood banks, diluted in Hanks Balanced Salts Solution (HBSS), and granulocytes were separated from mononuclear cells by centrifuging 30 ml of diluted cells through 20 ml of 64% Percoll in HBSS (2000 rpm, 20 min.) After aspirating mononuclear cells along with the supernatant, the pellet containing granulocytes was freed of contaminating erythrocytes by hypotonic lysis. Granulocytes were collected by centrifugation (1000 rpm, 10 min) and resuspended in PBS pH 7.0.

Subcellular Fractionation of Granulocytes

Isolated granulocytes in phosphate-buffered saline ($2 \times 10^7$ cells/ml) were treated with 5 mM diisopropylfluorophosphate (DFP) for 15 minutes at 4° C. The DFP-treated cells were centrifuged at $130 \times g$ for 10 minutes at 4° C., and the resulting pellet was resuspended in an ice-cold buffer containing 100 mM KCl, 3 mM NaCl, 1 mM ATP (Na)$_2$, 3.5 mM MgCl$_2$, and 10 mM Pipes, pH 7.3 (relaxation buffer). The cell suspension was disrupted by nitrogen cavitation for 20 minutes at 350 psi in a bomb (Parr Instrument Company, Moline, Illinois) at 4° C. and the cavitate was collected into the cat$^{2+}$ ion chelater EGTA, pH 7.4, at a final concentration of 1.5 mM. Nuclei and unbroken cells were pelleted (pl) by centrifugation at $500 \times g$ for 10 minutes at 4° C. The postnuclear supernatant (S1) was centrifuged for 15 minutes at 20,000 rpm (SS 34 rotor) on a discontinuous Percoll density gradient, as described for the isolation of azurophil granules (N. J. Borregaard, J. Cell Biol. 97: 52 (1983)). Fractions of approximately 1 ml were collected at 4° C. Percoll was removed from pooled azurophol granule fractions by centrifugation at 35,000 rpm ($180,000 \times g$) for 2 hours in an SW41 rotor. The layer that sedimented above the packed Percoll was resuspended in relaxation buffer and stored in aliquots at $-70°$ C.

Preparation of Granule Extracts

Fractions from the Percoll gradients corresponding to azurophil granules were pooled and Percoll was removed by centrifugation as described above. The granule preparation was resuspended in relaxation buffer and stored at $-70°$ C. The isolated granules were extracted with vigorous agitation in 0.05 M glycine-HCl buffer pH 2.0 for 40 minutes at 25° C. The acid-extract was centrifuged at $30,000 \times g$ for 20 minutes to obtain a soluble fraction The soluble fraction thus obtained was concentrated by centrifugation in Centricon 10 units (Amicon). The filtrate was used as starting material for chromatographic purification.

Microbicidal Assays

Microbicidal activity was routinely tested against Escherichia coli K12 (MC4100), Streptococcus faecalis (ATCC Accession No. 29212) and Candida albicans (clinical isolate). Organisms from a single colony on agar plates were inoculated into liquid medium and cultured overnight at 37° C. Aliquots of the overnight culture were inoculated into fresh nutrient broth and grown to mid-exponential phase. Cultures were then diluted into the test medium to the appropriate concentration.

Samples from reverse-phase liquid chromatography to be tested for microbicidal activity were dried by vacuum centrifugation in Immulon I microtire plates in the presence of 50 μl 0.1% BSA. Dried samples were resuspended in 0.1% acetic acid and returned to dryness by vacuum centrifugation. Samples were then resuspended in assay buffer and after appropriate dilutions of samples had been made, test organisms were added to the wells and incubation at 37.C was carried out for 30 to 60 minutes. Killing of all organisms was carried out in 20 mM phosphate pH 6, 0.25 M glucose and 0.02% Tween 20 unless otherwise indicated. A volume of the assay mixture corresponding to 200-300 organisms in the control assays were plated onto trypticase soy agar plates (*Escherichia coli* and *Streptococcus faecalis*) or spread onto Sabouraud dextrose agar plates (*Candida albicans*). Colony forming units were determined manually or by automated counting after overnight incubation at 37° C.

Characterization of Centricon Filtrates by Reverse-Phase, High Performance, Liquid Chromatography Trifluoracetic acid (TFA) was added to Centricon 10 Filtrates to 0.1% and the samples were applied to a Vydac wide pore C4 (250×4 mm) reverse-phase column and run on the gradient described below. Solvent A was 0.1% aqueous TFA and Solvent B was 0.1% TFA in HPLC grade acetonitrile. The gradient was as follows:

| TIME | % SOLVENT B |
| --- | --- |
| 0–2 minutes | 0% |
| 2–7 minutes | 0–15% |
| 7–67 minutes | 15–50% |
| 67–72 minutes | 50–100% |
| 72–75 minutes | 100% |

The equipment utilized was a Beckman HPLC system consisting of a Vydac wide pore C4 (250×4 mm) reverse-phase column, two 110B pumps, a 421A controller, a 210A injector, a 2 ml sample loop, a 163 variable wavelength detector, a 2112 Redirac fraction collector, and a Kipp and Zonen BD 41 chart recorder. The detector setting was 214 nm, 0–2.0 absorbance units full scale (AUFS) and the peak fractions were collected manually.

Sequence Analysis of Peak 1 and Peak 2 Peptides

Reversed phase HPLC purified Peak 1 and Peak 2 were concentrated to 50 microliters on a Speed Vac and loaded onto an Applied Biosystems 477A pulse liquid phase sequenator. Phenylthiohydantoin (PTH) analysis was performed on line using an Applied Biosystems Model 120A PTH Analyzer.

Amino Acid Analysis of Peak 1 and Peak 2

PTC amino acid analysis of polypeptides was obtained by 1 hour hydrolysis with 6.0 N HCl at 150° C. using a Waters Picotag system equipped with a Beckmal HPLC system.

Results

Granulocytes were isolated from buffy coats and protein was extracted from a Percoll-purified granule fraction as described in Methods. When this protein extract was concentrated by ultrafiltration in Centricon 10 units (Amicon), a filtrate was obtained which contained a portion of the low molecular weight proteins/peptides in the extract.

Figure 1:
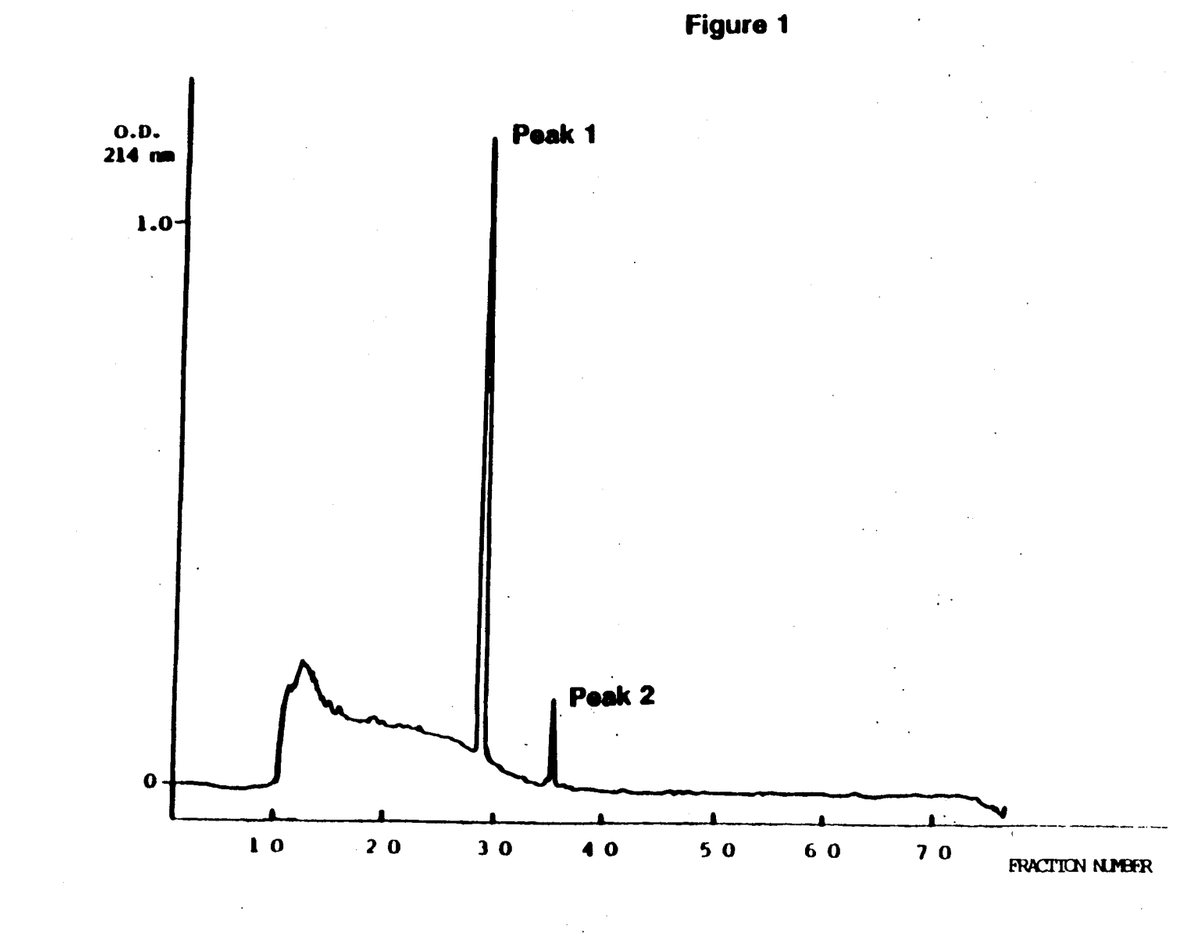
FIG. 1—High Performance Reverse-Phase Liquid Chromatography of Granulocyte Extracts Low molecular weight filtrates from acid extracts of isolated granules were subjected to reverse-phase chromatography as described in Methods. The positions of Peak 1 and Peak 2 are indicated.

This filtrate was analyzed by high performance reverse-phase liquid chromatography on a Vydac C4 column as described in Methods. Under these conditions, two major peaks were detected by absorbance at 214 nm (FIG. 1).

Figure 2:
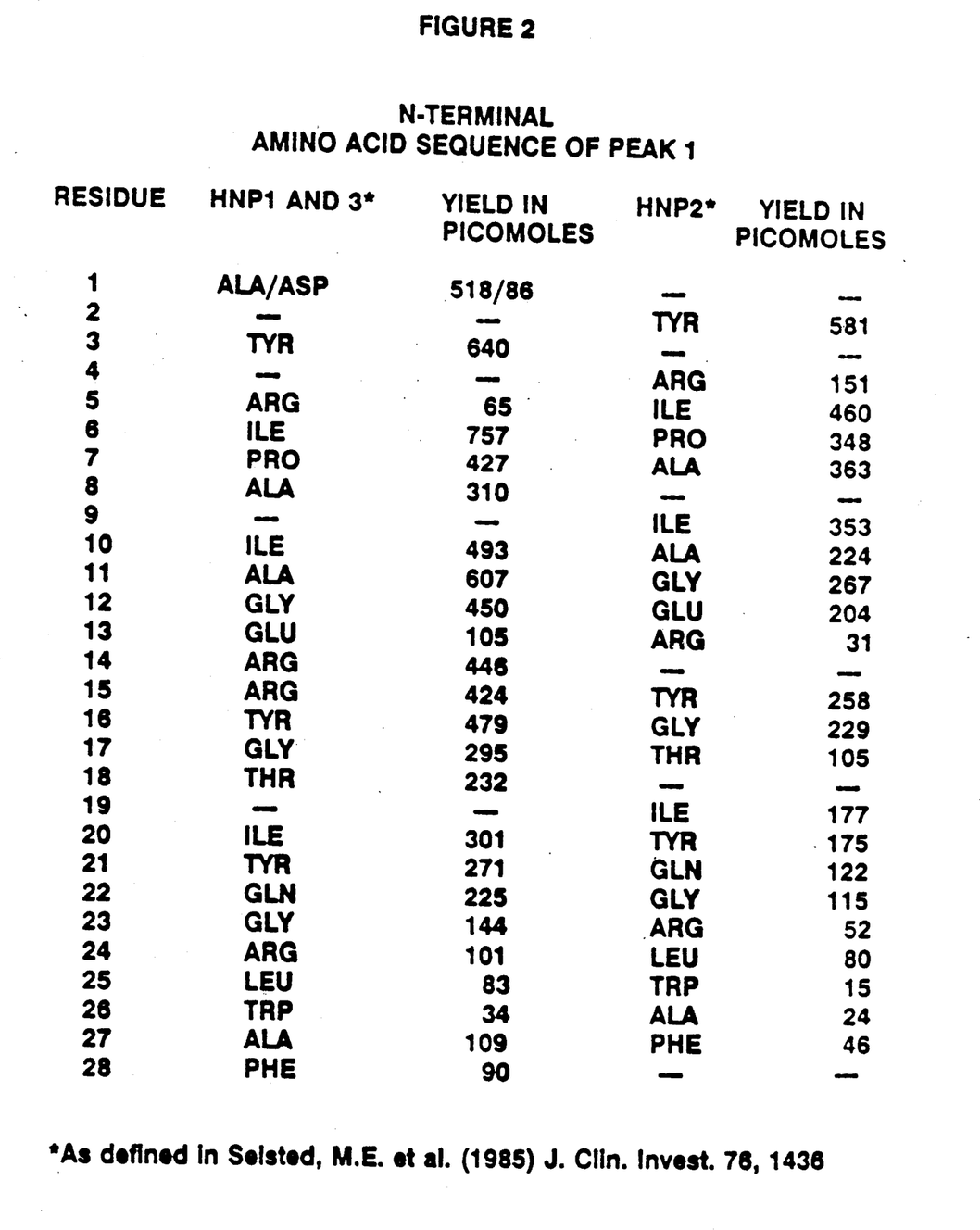
Figure 5:
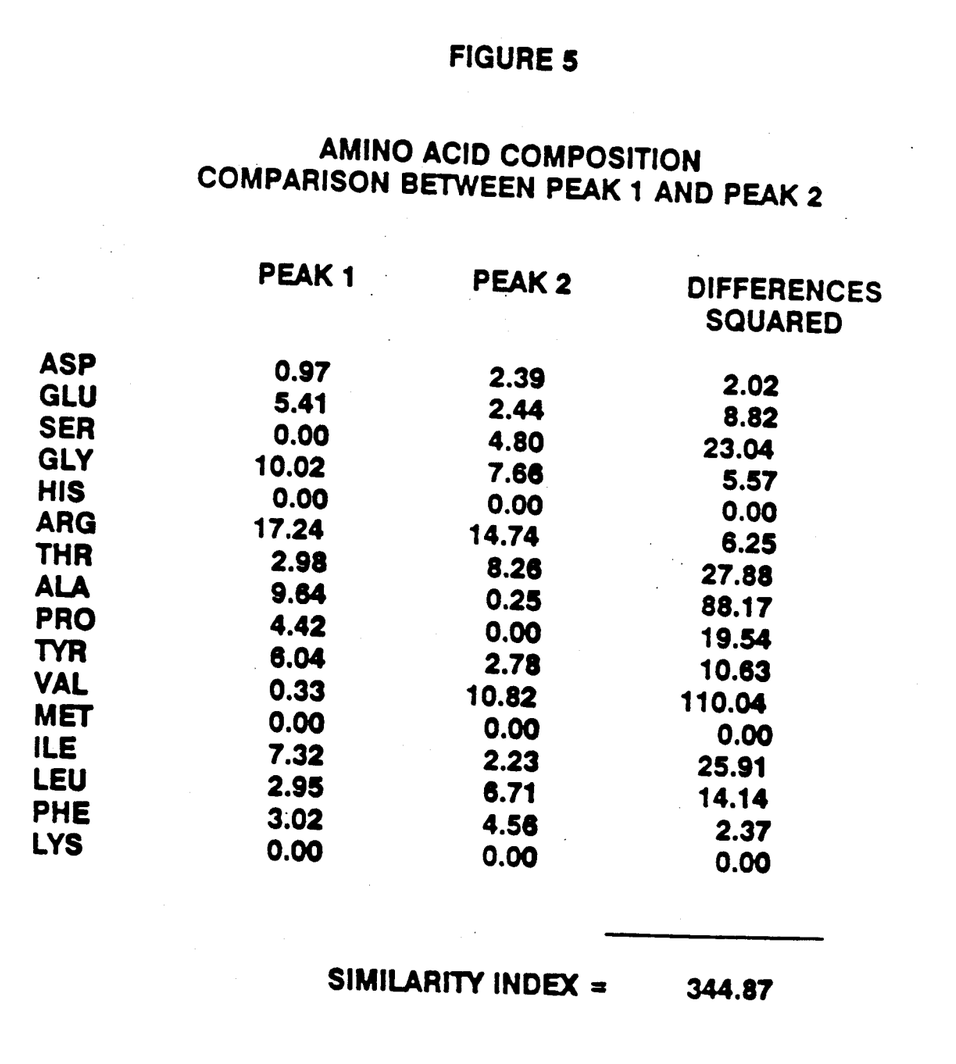
FIG. 5—Comparison of Amino Acid Compositions of Granulocyte Peak 2 and Human Defensin Amino acid composition of granulocyte Peak 2 and a mixture of human defensins (Peak 1) expressed as mole %. Similarity index=$\Sigma$ (difference mole %)$^2$ for each amino acid. Similarity index more than 100 usually indicates unrelated proteins (J. J. Marchalonis et al., Comp. Biochem. Physiol. 38: 609 (1971)).

When amino acid sequence analysis was performed as described in Methods, the early eluting peak (Peak 1) was determined to be a mixture of three known human defensins (FIG. 2). Estimating from N-terminal yields on sequencing, about 7% of the mixture was HNP3 and the remainder was almost evenly distributed between HNP1 (44%) and HNP2 (49%). Sequence analysis showed that the later eluting peak (Peak 2) contained the single sequence indicated in FIG. 3. Computer homology search of the Swiss Prox database (Intelligenetics) using the Needleman-Wunsch method identified the similarity between Peak 2 and the cysteine backbone of the human defensins (S. B. Needleman and D. D. Wunsch, J. Mol. Biol. 48: 443 (1970)). The sequence outside this cysteine backbone radically diverged from reported defensin sequences. Computer search failed to identify significant homology with any other known protein. Comparison of the amino acid compositions for Peak 1 and Peak 2 (FIG. 5) also demonstrates major differences between Peak 2 and Peak 1.

Figure 6:
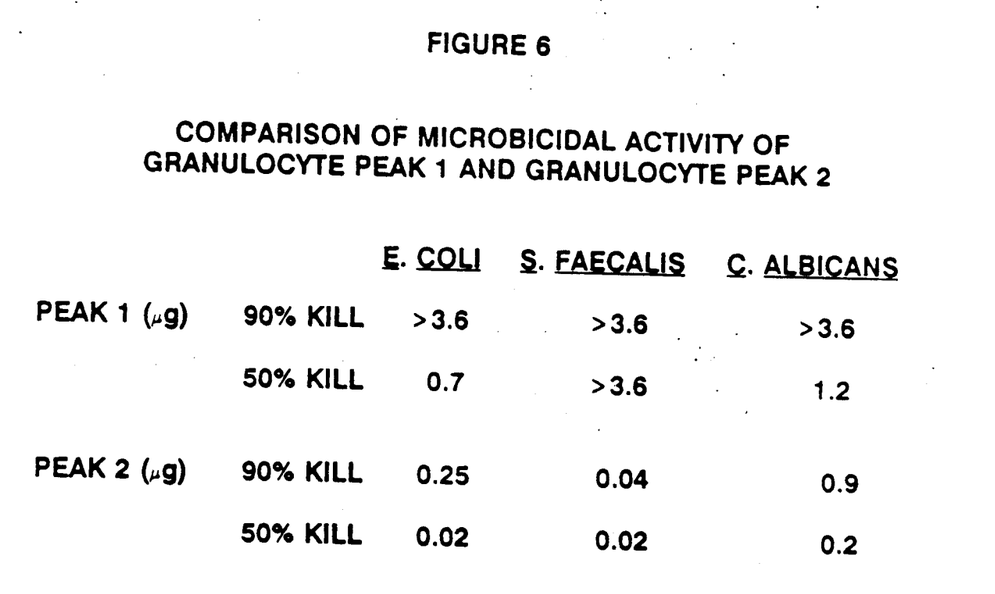

Aliquots of the reverse-phase peaks were tested for microbicidal activity in vitro against *Escherichia coli*, *Streptococcus faecalis* and *Candida albicans* as described in Methods. Protein concentrations in the samples were determined by amino acid composition analysis. The results (FIG. 6) clearly demonstrate that the Peak 2 peptide has much greater microbicidal activity than defensins (Peak 1). The higher specific activity of Peak 2 is particularly evident for activity against the gram positive organism *Streptococcus faecalis*, where the concentration required to reach the indicated levels of killing is about 100 fold less than for Peak 1. Peak 2 peptide is also more active against the gram negative bacteria *Escherichia coli* (15–30 fold) and the fungus *Candida albicans* (about 5 fold). It is clear that the altered sequence between Peak 2 and the defensins causes major alterations in bactericidal and fungicidal potencies.

Figure 7:
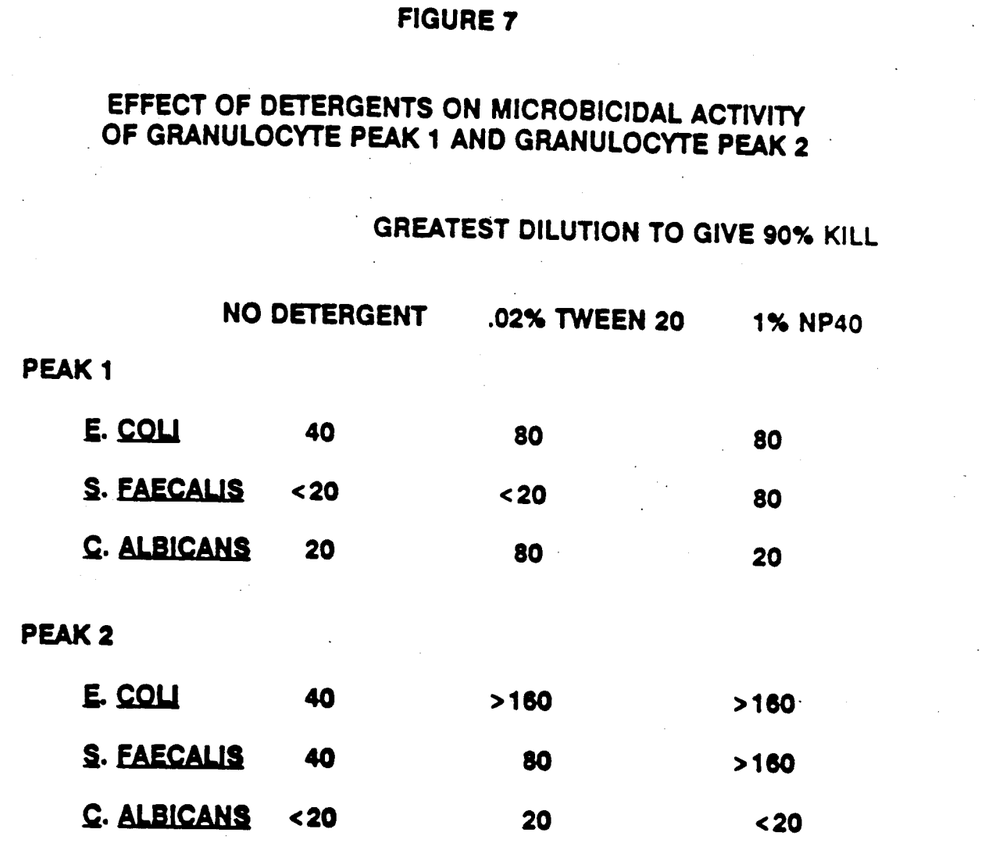

Additional studies were performed on the effects of the detergents Tween 20 and NP40 on the activities of Peak 1 and Peak 2 (FIG. 7). These detergents enhanced the activities of both peaks against bacteria and to a lesser extent against *Candida albicans*.

What is claimed is:

1. A purified polypeptide having the amino acid sequence NH$_2$-val-cys-ser-cys-arg-leu-val-phe-cys-arg-arg-thr-glu-leu-arg-val-gly-asn-cys-leu-ile-gly-gly-val-ser-phe-thr-cys-cys-thr-arg-val.

2. A composition which comprises the purified polypeptide of claim 1 in an amount effective to kill bacteria or fungi and a suitable carrier.

3. A method for killing bacteria or fungi which comprises contacting the bacteria or fungi with an effective amount of the composition of claim 2.

4. A composition of claim 2 which further comprises a detergent.

5. A composition of claim 4, wherein the detergent is nonionic.

6. A composition of claim 2, wherein the suitable carrier comprises a liposome.

* * * * *